(12) United States Patent
Popescu

(10) Patent No.: US 7,298,814 B2
(45) Date of Patent: Nov. 20, 2007

(54) IMAGING TOMOGRAPHY APPARATUS WITH MULTIPLE OPERATING MODES

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 337 days.

(21) Appl. No.: 11/148,769

(22) Filed: Jun. 9, 2005

(65) Prior Publication Data

US 2005/0281371 A1    Dec. 22, 2005

(30) Foreign Application Priority Data

Jun. 9, 2004    (DE)    ............... 10 2004 028 124

(51) Int. Cl.
*G01N 23/083* (2006.01)

(52) U.S. Cl. ............................. 378/9; 378/19

(58) Field of Classification Search ............... 378/9, 378/19, 4

See application file for complete search history.

(56) References Cited

U.S. PATENT DOCUMENTS

| 4,991,190 | A | 2/1991 | Mori | |
|---|---|---|---|---|
| 6,421,412 | B1 | 7/2002 | Hsieh et al. | |
| 2002/0090050 | A1* | 7/2002 | Nutt et al. | ............... 378/19 |
| 2005/0232389 | A1* | 10/2005 | Klingenbeck-Regn | ......... 378/9 |
| 2006/0165213 | A1* | 7/2006 | Hambuchen et al. | ......... 378/9 |

FOREIGN PATENT DOCUMENTS

DE    103 02 565    8/2004

* cited by examiner

*Primary Examiner*—Hoon Song
(74) *Attorney, Agent, or Firm*—Schiff Hardin LLP

(57) ABSTRACT

An imaging tomography apparatus with multiple operating modes has at least two radiators from which x-ray radiation emanates. The tomography apparatus has a radiation detector arrangement with a first detector and a second detector. At least the first detector can be reversibly moved relative to the second detector along a circumferential track of the measurement device of the gantry.

20 Claims, 2 Drawing Sheets

IMAGING TOMOGRAPHY APPARATUS WITH MULTIPLE OPERATING MODES

BACKGROUND OF THE INVENTION

1. Field of the Invention

The invention concerns an imaging tomography apparatus as well as a method for changing the operating mode of the tomography apparatus.

2. Description of the Prior Art

A tomography apparatus for imaging the heart is known from U.S. Pat. No. 6,421,412. This known tomography apparatus has a number of detector-radiator pairs. These are mounted offset from one another by a fixed angle around the z-axis. The geometry of the arrangement of each detector-radiator pair cannot be changed. In contrast to a conventional x-ray computed tomography apparatus, this tomography apparatus has smaller detectors and thus a smaller field of view, for example 200 mm as opposed to 500 mm. The field of application of this tomography apparatus is thereby limited to imaging the heart.

SUMMARY OF THE INVENTION

An object of the present invention is to remedy the disadvantages according to the prior art as represented by the above-described apparatus. In particular an optimally universally usable imaging tomography apparatus should be specified. It is a further object of the invention to provide an optimally simple method for changing the operating mode of such a tomography apparatus.

This object is achieved in accordance with the invention, having first and second x-ray radiators and a detector arrangement with a first detector and a second detector, wherein at least the first detector can be reversibly moved along a circumferential track of the measurement device of the gantry, relative to the second detector. It is thereby possible to position the detectors according to the requirements of a current operating mode selected for the tomography apparatus. A change between two operating modes of the tomography apparatus can be achieved by a reversible movement of at least the first detector, i.e. a movement of the detector in a forward direction or back direction. For example, no detectors need to be provided exclusively for one operating mode. It is thereby possible to reduce the total number of measurement channels of the detectors. The measurement channels of the detectors of the detector means can be optimally utilized. In particular it is possible to arrange the detectors such that all measurement channels for the detection of radiation can be used for every provided operating mode of the tomography apparatus. The acquisition and/or the processing of the measurement data can clearly be simplified significantly. For example, the data rate in the transfer of the measurement data to a data processing device can be reduced due to the lower number of measurement channels. In particular, no differentiation or filtering of used and unused measurement channels needs to ensue. Furthermore, the weight of the detector arrangement as well as the cost of the tomography apparatus can be reduced due to a lower number of measurement channels.

In a first measurement position, the respective detector surfaces of the first and second detectors are arranged to adjoin one another and an overall detector surface formed by these surfaces is aligned to a focus of one of the x-ray radiations of the tomography apparatus. In this measurement position, the tomography apparatus can be used as a conventional x-ray computed tomography apparatus. The measurement arrangement exhibits a field of view having a size or diameter that is determined by the size of the overall detector surface. For example, a field of view of approximately 499 mm can be achieved.

In a second measurement position, the first detector is arranged opposite the second radiator and the second detector is arranged opposite the first radiator.

According to an embodiment of the tomography apparatus, the first radiator can be reversibly moved on the circumferential track relative to the second radiator. For example, it is thereby possible to achieve a change between two operating modes of the tomography apparatus by moving the first detector and the first radiator. For example, a change from the operating mode of a conventional computed tomography apparatus to an operating mode suitable for imaging the heart can be implemented as follows:

At the outset, the overall detector surface formed by the detector surfaces of the first detector and second detector is aligned to the focus of the first radiator. The first detector is subsequently moved such that its detector surface detects a ray fan originating from the second radiator and the first radiator is moved such that a ray fan originating from this can be detected by the detector surface of the second detector.

The original operating mode can be re-set by a reversible movement. The change can be implemented in a simple manner.

According to a further embodiment of the invention, the first radiator and the second radiator are mounted fixed on the measurement device offset from one another by a predetermined angle. A change of the operating mode can ensue by a movement of the first and second detectors. The first and second radiators preferably are mounted offset from one another by an angle of approximately 90 degrees. The fixed angle, for example, can be half of the aperture angle of a ray fan originating from the second radiator. This arrangement of the radiators is particularly suitable for the operating modes of a conventional x-ray computed tomography apparatus and for imaging with increased resolution, for example for imaging the heart.

According to a further embodiment, the first detector and the second detector can be reversibly, respectively moved on a circumferential track. For example, it is possible to reversibly move the second detector to the location of the first radiator. The second detector is thereby moved along the circumferential track such that its detector surface is aligned to the focus of the first radiator. The detector surface of the first detector is analogously aligned to the focus of the second radiator.

The circumferential track is preferably a circular track relative to the z-axis or an axis parallel thereto. Movement of a radiator and/or detector along such a circular track is possible in a simple manner. Furthermore, circular tracks are, for example, particularly well suited for movement of the detector and/or radiator on the gantry of an x-ray computed tomography apparatus.

In a further embodiment of the invention, at least one of the detectors and/or radiators can be rotated around an axis running parallel to the z-axis. It is thus possible to move the detector and/or the radiator on a circumferential track and additionally to rotate the detector and/or radiator around an axis. The axis preferably runs through the detector or radiator. The detector and/or radiator thus can be moved in two dimensions. It is thereby possible in a simple manner to rotate the detector or the radiator such that the detector surface of the detector and the radiator are ideally aligned to one another. For example, the detector surface can be aligned to the focus of the radiator. An optimal alignment of detector and radiator enables an increase in the quality of the measurement data.

In another embodiment of the invention, an arrangement is provided for automatic movement of at least one of the detectors or radiators. A change from one operating module to another thus can be implemented quickly and precisely in a simple manner. The change can ensue without intervention of the operator of the tomography apparatus. Possible sources of error in the change can be reduced. The arrangement for movement is appropriately formed electromechanical actuators. For an automatic movement of a detector or radiator, it is furthermore advantageous to control the actuators a computer program. The precision of the positioning of the detectors and/or radiators, in particular the alignment to the focus of a radiator, can ensue reliably, quickly and exactly.

According to a further embodiment, the first detector and the second detector have respective detector surfaces that are symmetric to one another. Due to the symmetry, for example the same size and the same number of measurement channels, the processing of the measurement data can be implemented in an analogous manner for both detector surfaces. In particular, given an arrangement of the first detector opposite the second radiator and of the second detector opposite the first radiator, two identical detector-radiator pairs can be achieved. This is particularly advantageous for the acquisition of measurement data.

According to a variant of the invention, in the first measurement position the first and second detectors are symmetrically arranged with regard to a plane running through the detector arrangement. This simplifies the data acquisition and the data processing. For example, no different angles of incidence of the x-ray radiation on the detector surfaces need to be considered.

In a further embodiment of the invention, in the second measurement position the first detector is arranged opposite the second radiator and the second detector is arranged opposite the first radiator, and the first and second detectors as well as the first and second radiators are arranged azimuthally offset from one another by an angle relative to the z-axis. A higher temporal resolution can be achieved with this measurement position compared to the first measurement position. This is particularly enabled by the azimuthally offset arrangement of radiators and detectors. This second measurement position is particularly suitable for imaging moving subjects, for example the heart. In the second measurement arrangement, the first radiator and the second detector and the second radiator and the first detector exhibit a common field of view, for example with a diameter of approximately 256 mm. If, for example, the first detector and the second detector are symmetrically arranged and possess equally large detector surfaces, the field of view is circular and centered on the z-axis. This is particularly advantageous for a measurement device rotating around the z-axis.

In another embodiment of the invention, at least one of the radiators has a device for adjustment of an aperture angle for a ray fan originating from said radiator. It is thereby possible to adapt the expansion (widening) of the ray fan to the size of a detector surface mounted opposite the radiator. The quality of the measurement data thus can be increased and a reduction of the radiation exposure of an examination subject can be achieved. The device for adjustment of the aperture angle is preferably a diaphragm. Alternatively, the device for adjustment of the aperture angle can be a phi collimator. If the detector surface opposite a radiator changes for various operating modes, it is advantageous, for example, to use a diaphragm with a variable aperture angle. Otherwise a diaphragm with a fixed aperture angle can be used. Furthermore, it is possible to adapt the field of view of the tomography apparatus to a subject to be examined with a device for adjustment of an aperture angle. An unnecessary radiation exposure of one of the subjects can be prevented.

In another embodiment of the invention, the first detector and the second detector share a common system for data acquisition and processing. This enables a simplified acquisition and processing of the data. The measurement data of the first detector and the second detector can be synchronized and combined in a simple manner. In particular the reconstruction of x-ray images can be simplified. Reconfiguration of the system can be avoided given a change of the operating mode. In particular it is possible to transfer the measurement data from the rotatable measurement device to a data processing unit via an operating system that is common to both detectors. A separate transfer system is not necessary for each detector. Furthermore, the weight of the tomography apparatus can be reduced by using such a common system for data acquisition and processing. For example, the centrifugal force acting on the measurement device rotatable around a fixed z-axis of a gantry of an x-ray computed tomography apparatus can be reduced.

In a further embodiment of the invention, the detector surfaces are curved in the φ-direction or planar. The (φ-direction, as is conventional in computed tomography terminology, is the direction of the unit vector belonging to the angle coordinates of a cylindrical coordinate system, the coordinate axis of the cylindrical coordinate system proceeding parallel to the z-axis. For example, the coordinate axis can be the z-axis or can run through a focus of a radiator. The imaging tomography apparatus is not limited to a specific shape of the detector surface or detector type. For example, detectors can be used with a detector surface curved in the (φ-direction and a number of detector rows disposed in series in the direction of the z-axis. Furthermore, it is possible to use detectors with detector surfaces that are planar, known as flat detectors.

The invention also encompasses a method for changing from a first operating mode of an imaging tomography apparatus (in particular an x-ray computed tomography apparatus) to a second operating mode, wherein the detector arrangement has a first detector and a second detector, and whereby to change the operating mode at least the first detector is moved along a circumferential track of the measurement device of the gantry from a first measurement position into a second measurement position, relative to the first detector. The advantageous properties of the described tomography apparatus are applicable as well to the method

DESCRIPTION OF THE PREFERRED EMBODIMENTS

Figure 1:
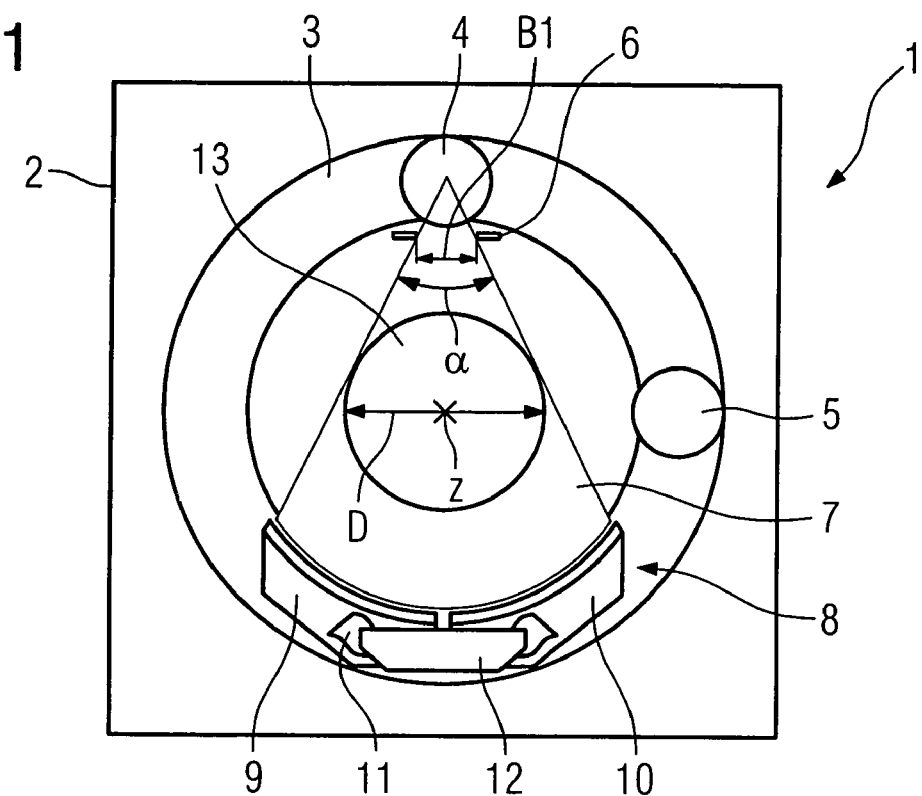
FIG. 1 schematically illustrates a computed tomography apparatus in accordance with the invention with the radiation detectors in a first measurement position.

The inventive computed tomography apparatus in a first measurement position is shown in FIG. 1. A gantry (designated with the reference character 1) of the apparatus has a stationary part 2 and a part 3 that can rotate around a fixed z-axis z. A first x-ray tube 4 and a second x-ray tube 5 are mounted on the rotatable part 3 offset from one another by an angle of approximately 90° with regard to the z-axis z. A diaphragm mounted on the first x-ray tube 4, with a variable first diaphragm aperture B1, is designated with the reference character 6. A fan-shaped x-ray beam 7 with an aperture angle $\alpha$ originates from the first x-ray tube 4. A detector arrangement 8 is located on the rotatable part 3 of the gantry 1 in the beam path of the first x-ray beam 7 opposite the first x-ray tube 4. The detector means 8 has a first detector 9 and a second detector 10 disposed adjacent to one another. The first detector 9 and the second detector 10 are connected with flexible lines 11 with a data acquisition unit 12. A field of view with a diameter D, situated in the beam path of the first x-ray beam 7, is designated with the reference character 13.

The functioning of the tomography apparatus is as follows:

The fan-shaped x-ray beam 7 emanates from the first x-ray tube 4 in the operation of the x-ray computed tomography apparatus. The x-ray tube 5 is inoperative. To detect the x-ray beam 7, the first detector 9 and the second detector 10 are arranged next to one another in its beam path. They form an essentially contiguous detection surface azimuthally curved with regard to the z-axis z. Each detector 9 or and 10 has one or more (lying in series) detector rows in the direction of the z-axis z. All channels of the first detector 9 and the second detector 10 are used to detect the x-ray radiation 7. This is possible with an aperture angle of, for example, $\alpha=52°$ suitably set by the diaphragm 6. The diameter D of the field of view 13 is maximum at this aperture angle. The diameter D of, for example, 499 mm corresponds to that of a field of view of a conventional x-ray computed tomography apparatus. The apparatus of FIG. 1 can be operated as such a conventional x-ray computed tomography apparatus in the operating mode. For acquisition and further processing of the data, the first detector 9 and the second detector 10 share a common data acquisition unit 12. This synchronizes the data acquired by the detectors 9 and 10 and combines these in a correct sequence. The data acquisition unit 12 forwards the data to a transfer device (not shown) that transfers the data from the rotatable part 3 of the gantry 1 to the stationary part 2 of the gantry.

Figure 2:
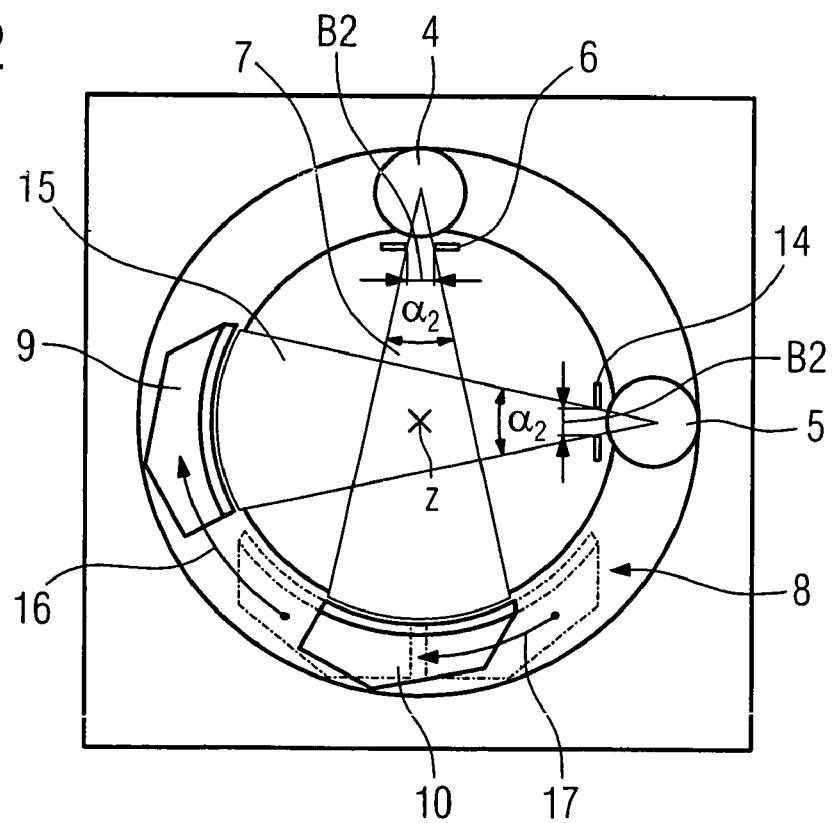
FIG. 2 schematically illustrates the computed tomography apparatus of FIG. 1 showing how the radiation detectors are changed from the first measurement position to a second measurement position.

FIG. 2 schematically illustrates the changing of the positions of the first detector 9 and second detector 10. The first x-ray tube 4 and the second x-ray tube 5 are disposed as in FIG. 1, offset by approximately 90°. The positions of the first detector 9 and second detector 10 of FIG. 1 is shown only for explanation. The diaphragm 6 with a second diaphragm aperture B2 and the second detector 10 are located in succession in the beam path of the first x-ray beam 7 emanating from the first x-ray tube 4 with a second aperture angle $\alpha_2$. A second diaphragm 14 with the fixed second diaphragm aperture B2 and the second detector 9 are located in succession in a beam path of a second x-ray beam 15 emanating from the first x-ray tube 5 with a second aperture angle $\alpha_2$. Position changes of the first detector 9 and second detector 10 relative to the position (shown in FIG. 1) are shown with the reference characters 16 and 17.

The position changes of the first detector 9 and second detector 10 ensue as follows:

The first detector 9 and the second detector 10 are positioned by means of electromechanical actuators (not shown). The actuators are connected to a control system (not shown) of the gantry 1 and are controlled by software For the positioning, the first detector 9 is rotated (moved on the track) clockwise by the angle $90-\alpha_2/2$ degrees relative to the z-axis z. The first detector 9 is subsequently rotated clockwise around an axis running through the detector and thus aligned to the focal spot of the second x-ray tube 5. The second detector 10 is rotated clockwise by the angle $\alpha_2/2$ degrees around a rotation axis running through the focal spot of the first x-ray tube 4 and parallel to the z-axis z. The second detector 10 is thereby aligned to the focal spot of the first x-ray tube 4. The diaphragm apertures B2 of the diaphragms 6 and 14 are selected such that the x-ray beams 7 and 15 respectively emanating from the first x-ray tube 4 and the second x-ray tube 5 are entirely detected by the second detector 10 and the first detector 9, respectively.

Figure 3:
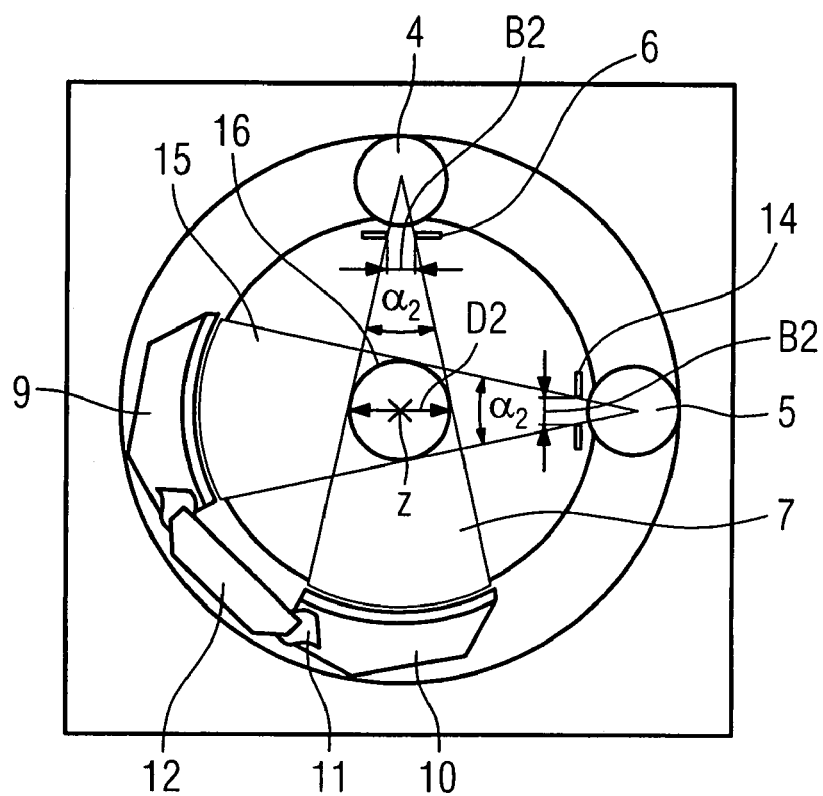
FIG. 3 schematically illustrates the computed tomography apparatus of FIGS. 1 and 2 with the radiation detectors in the second measurement position.

A second measurement position is shown in FIG. 3. The arrangement of the first x-ray tube 4 and second x-ray tube 5 as well as the position of the first detector 9 and second detector 10 correspond to those in FIG. 2. The first detector 9 and the second detector 10 are connected with the data acquisition unit 12 with the flexible line 11. This data acquisition unit 12 is located between the two detectors 9 and 10. A common field of view 16 has a second diameter D2, and is situated in the beam paths of the first x-ray beam 7 and the second x-ray beam 15.

The functioning of the tomography apparatus is as follows:

After the positioning (as described in FIG. 2) of the first detector 9 and second detector 10, these are aligned to the focal spots of the second x-ray tube 5 and the first x-ray tube 4, respectively. The optical axes of the first x-ray tube 4 and of the second detector 10, and of the second x-ray tube 5 and the first detector 9, intersect in the region of the z-axis z and are essentially perpendicular to one another. The second detector 10 detects the x-ray beam 7 emanating from the first x-ray tube 4. The first detector 9 detects the x-ray beam 15 emanating from the second x-ray tube 5. The size of the field of view 16 is smaller in comparison with the field of view 13 of FIG. 1. The field of view 16 is established by the azimuthal expansion (dimension) of the first detector 9 and second detector 10 as well as by the aperture angle $\alpha_2$. With an aperture angle of, for example, 26 degrees, it is possible to achieve a second field of view 16 with a second diameter D2 of approximately 256 mm. This is sufficient in order to use the x-ray computed tomography apparatus for imaging of heart. The first detector 9 and second detector 10 are connected with the common data acquisition unit 12 via flexible cables. It is thereby possible to move the first detector 9 and the second detector 10 relative to the data acquisition unit 12. The data acquisition unit 12 processes the data and prepares the transfer of the data from the rotatable part 3 of the gantry 1 to the stationary part 2 of the gantry 1.

Figure 4:
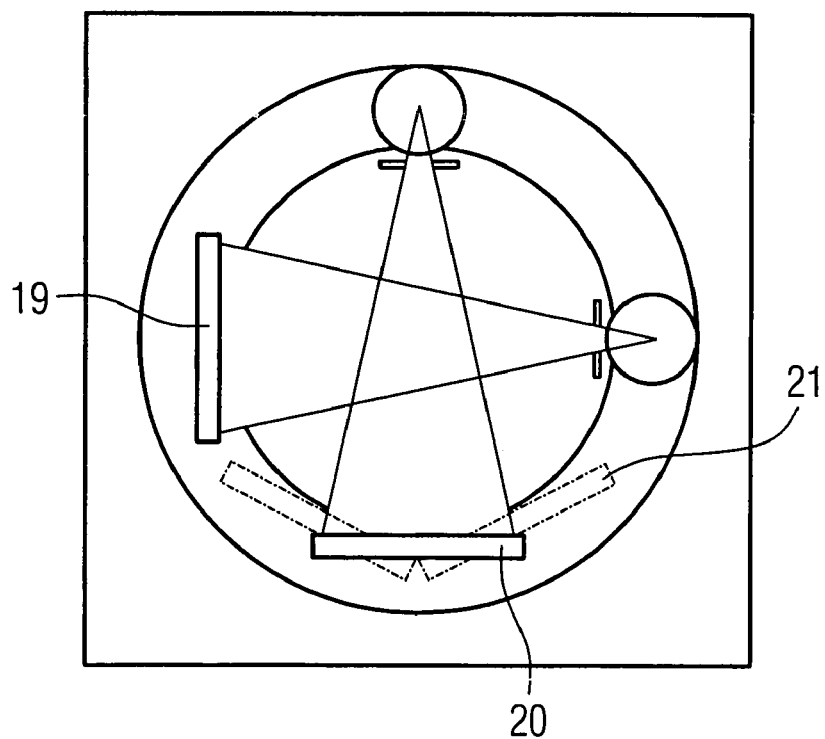
FIG. 4 schematically illustrates a computed tomography apparatus in accordance with the invention with the radiation detectors formed as flat panel detectors.

FIG. 4 shows a measurement arrangement analogous to FIG. 3, with a second detector arrangement 21 formed of a first flat detector 19 and a second flat detector 20. The first and second detectors 9, 10 shown in FIG. 1 through FIG. 3 with azimuthally curved detector surfaces are replaced by flat detectors. The functioning as well as the positioning of the first flat detector 19 and the second flat detector 20 are analogous to those explained in connection with FIG. 1 through FIG. 3.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray computed tomography apparatus comprising:
a gantry having a measurement device rotatable around a rotational axis;
said measurement device comprising a first x-ray radiator, a second x-ray radiator, and a detector arrangement to detect x-rays emanating from said first x-ray radiator and said second x-ray radiator; and
said detector arrangement comprising a first detector having a detector surface and a second detector having a detector surface, and a track, mounted at said measurement device, along which each of said first and second detectors is movable, said first and second detectors being movable along said track to a first measurement position wherein the detector surface of said first detector and the detector surface of said second detector are disposed adjacent to each other forming an overall detector surface aligned to a focus of one of said first and second x-ray radiators, and being movable to a second position wherein the first detector is disposed opposite said second x-ray radiator on said measurement device and wherein said second detector is disposed opposite said first x-ray radiator on said measurement device.

2. A computed tomography apparatus as claimed in claim 1 wherein said first and second x-ray radiators are also movable along said circumferential track, with said first x-ray radiator being reversibly movable on said circumferential track relative to said second x-ray radiator.

3. A computed tomography apparatus as claimed in claim 1 wherein said first x-ray radiator and said second x-ray radiator are mounted at said measurement device offset from each other by a predetermined angle.

4. A computed tomography apparatus as claimed in claim 1 wherein said first detector and said second detector are reversibly movable on a single circumferential track.

5. A computed tomography apparatus as claimed in claim 1 wherein said circumferential track comprises a circular track with respect to said rotational axis for an axis parallel thereto.

6. A computed tomography apparatus as claimed in claim 1 wherein at least one of said first detector, said second detector, said first x-ray radiator and said second x-ray radiator is rotatable around an axis proceeding parallel to said rotational axis.

7. A computed tomography apparatus as claimed in claim 1 comprising an arrangement for automatically moving at least one of said first detector and said second detector along said circumferential track.

8. A computed tomography apparatus as claimed in claim 7 wherein said first x-ray radiator and said second x-ray radiator also are movable along said circumferential track, and comprising an arrangement for automatically moving at least one of said first detector, said second detector, said first x-ray radiator and said second x-ray radiator along said circumferential track.

9. A computed tomography apparatus as claimed in claim 7 wherein said arrangement for automatically moving comprises electromechanical actuators.

10. A computed tomography apparatus as claimed in claim 9 wherein said arrangement comprises a control unit for operating said actuators, controlled by a computer program.

11. A computed tomography apparatus as claimed in claim 1 wherein said detector surface of said first detector and said detector surface of said second detector are symmetrical with respect to each other.

12. A computed tomography apparatus as claimed in claim 1 wherein, in said first measurement position, said first detector and said second detector are disposed symmetrically relative to a plane proceeding through said detector arrangement.

13. A computed tomography apparatus as claimed in claim 1 wherein, in said second measurement position, said first detector, said second detector, said first x-ray radiator and said second x-ray radiator are each disposed azimuthally offset from each other by an angle.

14. A computed tomography apparatus as claimed in claim 1 wherein at least one of said first x-ray radiator and said second x-ray radiator comprises a device for adjusting an aperture angle of a radiation beam emanating therefrom.

15. A computed tomography apparatus as claimed in claim 14 wherein said device for adjusting said aperture angle is a diaphragm.

16. A computed tomography apparatus as claimed in claim 14 wherein said device for adjusting said aperture angle is a phi collimator.

17. A computed tomography apparatus as claimed in claim 1 comprising a system for data acquisition and processing connected to and share by said first detector and said second detector.

18. A computed tomography apparatus as claimed in claim 1 wherein said detector surface of said first detector and said detector surface of said second detector are each azimuthally curved.

19. A computed tomography apparatus as claimed in claim 1 wherein said detector surface of said first detector and said detector surface of said second detector are each planar.

20. In an x-ray computed tomography apparatus comprising a first x-ray radiator, a second x-ray radiator, a first detector and a second detector for detecting radiation emitted by said first x-ray radiator and said second x-ray radiator, each of said first detector and said second detector having a detector surface, said first detector and said second detector being mounted on a circumferential track of a measurement device that is rotatable around a rotational axis in a gantry, said first x-ray radiator and said second x-ray radiator also being mounted on said measurement device, a method for changing between a first operating mode of the computed tomography apparatus and a second operating mode of the computed tomography apparatus comprising the steps of:
in said first operating mode, moving said first and second detectors along said circumferential track to position said detector surface of said first detector adjacent to said detector surface of said second detector to form an overall detector surface aligned to a focus of one of said first x-ray radiator and said second x-ray radiator; and
in said second operating mode, moving said first detector along said track to a location opposite said second x-ray radiator and moving said second detector along said circumferential track to a position opposite said first x-ray radiator.

* * * * *